United States Patent
Niibe

(10) Patent No.: US 11,058,387 B2
(45) Date of Patent: Jul. 13, 2021

(54) RADIOGRAPHIC APPARATUS, AND AREA DOSE OBTAINING APPARATUS AND METHOD

(71) Applicant: CANON KABUSHIKI KAISHA, Tokyo (JP)

(72) Inventor: Yusuke Niibe, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 47 days.

(21) Appl. No.: 16/392,896

(22) Filed: Apr. 24, 2019

(65) Prior Publication Data
US 2019/0328350 A1 Oct. 31, 2019

(30) Foreign Application Priority Data

Apr. 26, 2018 (JP) .............................. JP2018-085721

(51) Int. Cl.
*A61B 6/00* (2006.01)
*G06T 7/00* (2017.01)
*G06T 7/70* (2017.01)

(52) U.S. Cl.
CPC .......... *A61B 6/5241* (2013.01); *A61B 6/4266* (2013.01); *G06T 7/0012* (2013.01); *G06T 7/70* (2017.01); *G06T 2207/10116* (2013.01)

(58) Field of Classification Search
CPC combination set(s) only.
See application file for complete search history.

(56) References Cited

U.S. PATENT DOCUMENTS

| | | | |
|---|---|---|---|
| 6,422,751 B1 | 7/2002 | Aufrichtig et al. | |
| 6,563,943 B1* | 5/2003 | Sasada | G06T 3/4038 382/132 |
| 6,748,049 B1* | 6/2004 | Yamamoto | H04N 3/1593 378/98.7 |
| 7,110,495 B2 | 9/2006 | Tamegai | |
| 2004/0247081 A1* | 12/2004 | Halsmer | A61B 6/544 378/108 |
| 2005/0129298 A1* | 6/2005 | Warp | A61B 6/5241 382/132 |
| 2005/0213849 A1* | 9/2005 | Kreang-Arekul | G06T 5/008 382/284 |
| 2010/0172567 A1* | 7/2010 | Prokoski | A61B 5/418 382/132 |

(Continued)

FOREIGN PATENT DOCUMENTS

JP 3133741 B 2/2001
JP 2009-142497 A 7/2009

(Continued)

*Primary Examiner* — Tsung Yin Tsai
(74) *Attorney, Agent, or Firm* — Venable LLP

(57) ABSTRACT

A radiographic apparatus, comprises a generating unit that generates a composite image using a plurality of radiographic images that have been obtained by a plurality of radiation detecting apparatuses through single radiation irradiation by a radiation generating unit, a determining unit that determines a region to be analyzed so as to eliminate an overlap in an overlapping portion arising from a spatial placement of the plurality of radiation detecting apparatuses, and an obtaining unit that obtains an area dose for the composite image by obtaining an area dose for the region to be analyzed determined by the determining unit.

12 Claims, 10 Drawing Sheets

(56) References Cited

U.S. PATENT DOCUMENTS

| | | | | |
|---|---|---|---|---|
| 2011/0064193 | A1* | 3/2011 | Minnigh | A61B 6/505 |
| | | | | 378/62 |
| 2014/0219420 | A1* | 8/2014 | Ishikawa | A61B 6/5241 |
| | | | | 378/62 |
| 2016/0035451 | A1* | 2/2016 | Tsuji | A61B 6/4266 |
| | | | | 378/62 |
| 2016/0220213 | A1* | 8/2016 | Miyamoto | H04N 5/367 |
| 2016/0249870 | A1* | 9/2016 | Tajima | A61B 6/4291 |
| | | | | 378/62 |
| 2016/0287195 | A1* | 10/2016 | Tagawa | A61B 6/08 |
| 2016/0287202 | A1* | 10/2016 | Miyachi | A61B 6/5241 |
| 2016/0302755 | A1* | 10/2016 | Takagi | A61B 6/582 |
| 2017/0084025 | A1* | 3/2017 | Lyu | G06K 9/00 |
| 2017/0143286 | A1* | 5/2017 | Exelmans | A61B 6/548 |
| 2017/0296133 | A1* | 10/2017 | Katsumata | A61B 6/5294 |
| 2018/0008224 | A1* | 1/2018 | Arima | G06T 7/0012 |
| 2018/0108118 | A1* | 4/2018 | Takahashi | G06T 5/005 |
| 2018/0260966 | A1* | 9/2018 | Omi | G06T 7/32 |

FOREIGN PATENT DOCUMENTS

| | | |
|---|---|---|
| JP | 4387644 B | 12/2009 |
| JP | 4708559 B | 6/2011 |

* cited by examiner

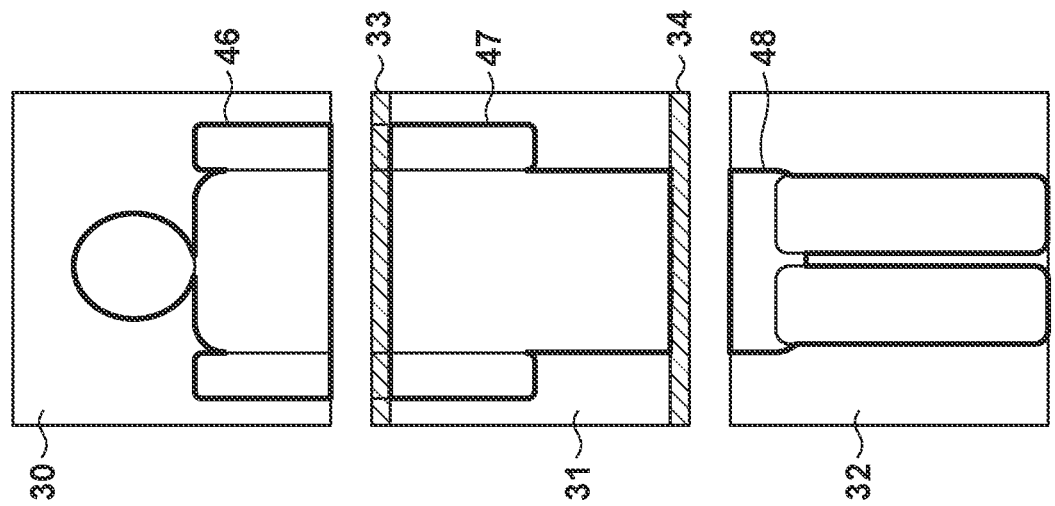
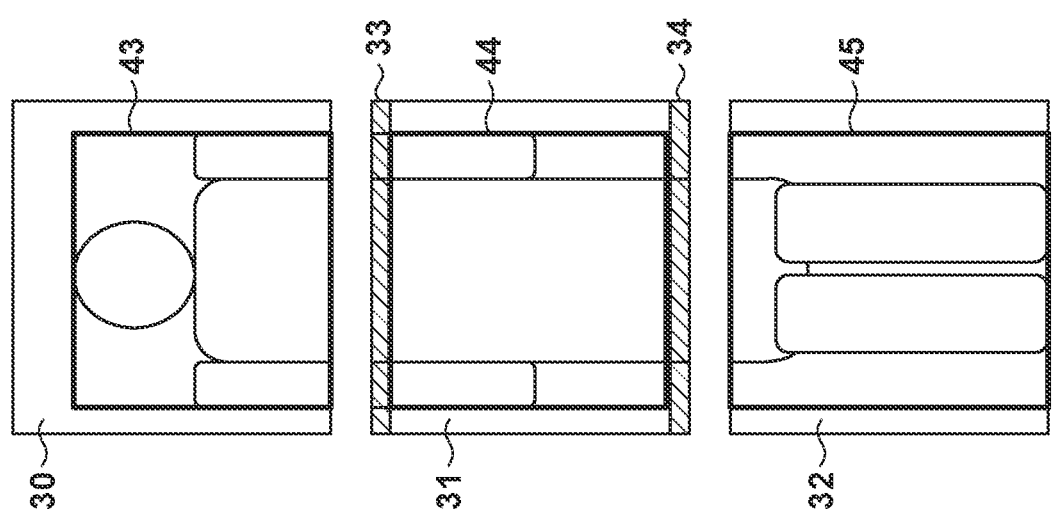
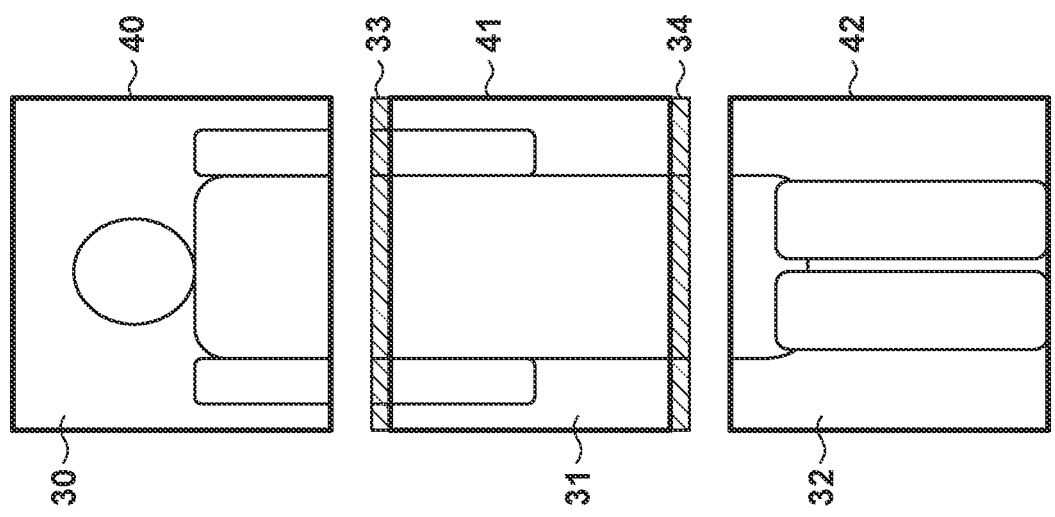

5a

| IMAGE ID | DAP | TUBE VOLTAGE | TUBE CURRENT | IRRADIATION PERIOD |
|---|---|---|---|---|
| 001 | 105 | V1 | I1 | T1 |
| 002 | 110 | | | |
| 003 | 100 | | | |

5b

| IMAGE ID | DAP | TUBE VOLTAGE | TUBE CURRENT | IRRADIATION PERIOD |
|---|---|---|---|---|
| 004 | 315 | V1 | I1 | T1 |

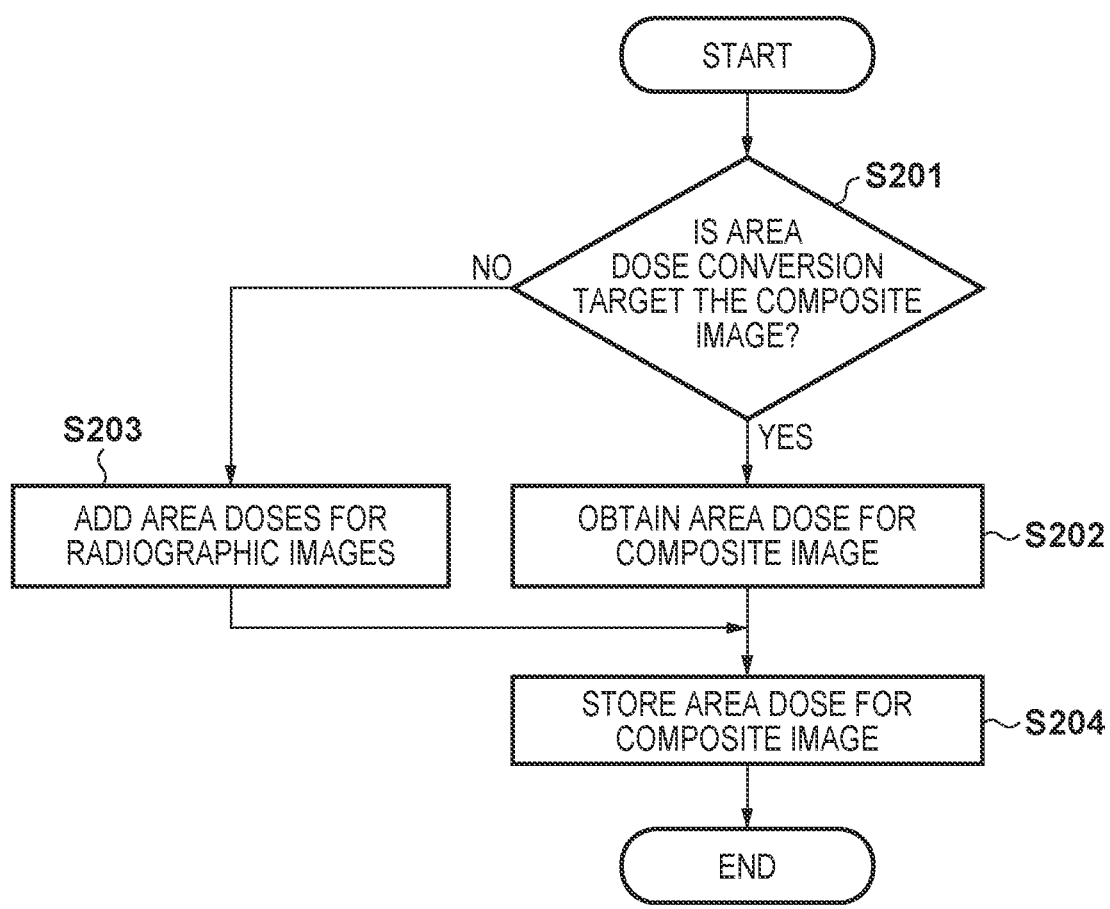

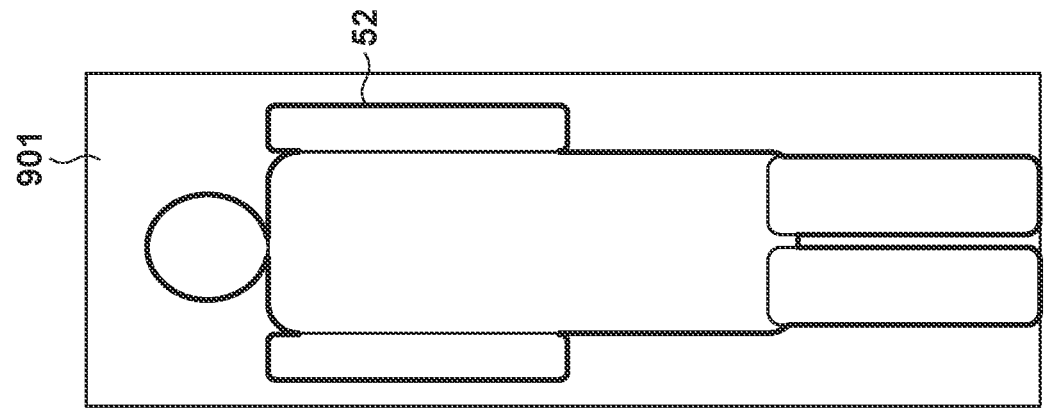
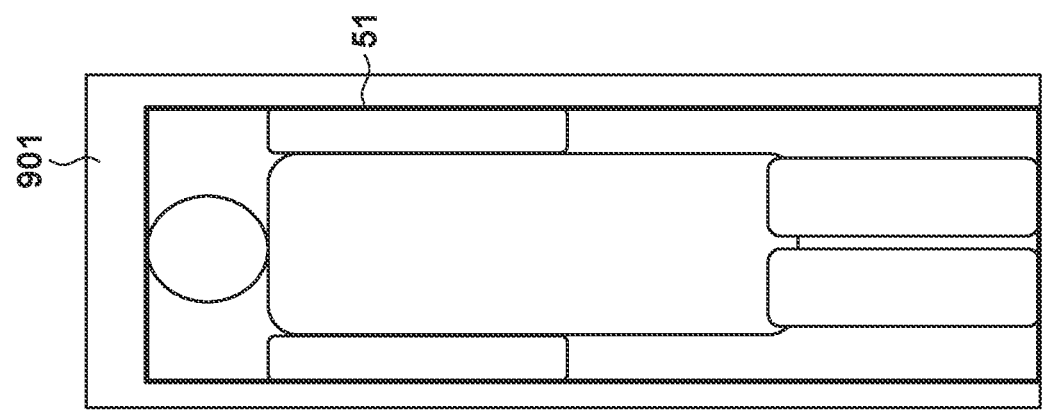
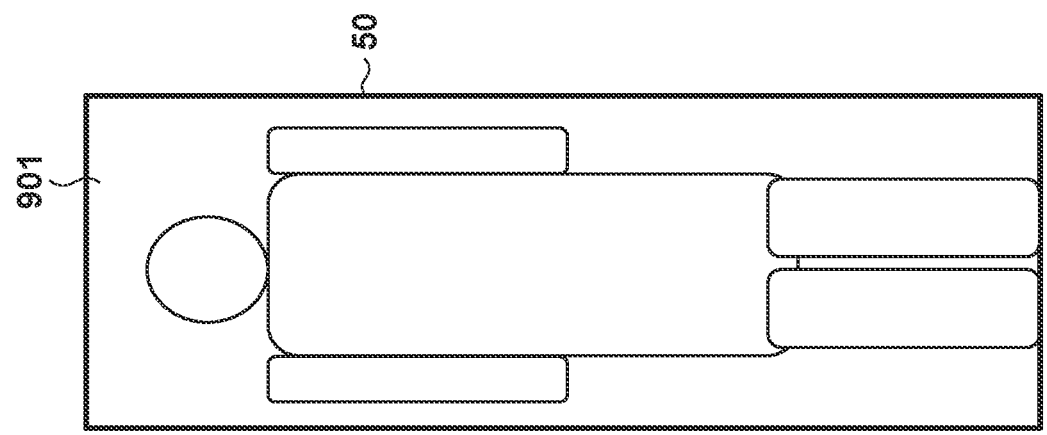

RADIOGRAPHIC APPARATUS, AND AREA DOSE OBTAINING APPARATUS AND METHOD

BACKGROUND OF THE INVENTION

Field of the Invention

The present invention relates to a radiographic apparatus, and an area dose obtaining apparatus and method.

Description of the Related Art

There is a known radiographic system including a radiation generating unit that irradiates an object with radiation (e.g., X-rays), and a radiation detecting apparatus that detects the intensity distribution of radiation that has passed through this object and obtains a radiographic image of the object. In recent years, as the importance of management of a radiation exposure dose on an object has been recognized, display of an area dose is required in such a radiographic system. An area dose is measured by installing an area dose meter.

To reduce a cost increase attributed to the installation of an area dose meter, or for a radiographic system in which the installation of an area dose meter is difficult, a radiographic system that enables dose calculation without mounting an area dose meter has been suggested. Japanese Patent Laid-Open No. 2009-142497 and Japanese Patent No. 3133741 use a simple dose conversion method, such as a Non Dosimeter Dosimetry (NDD) method, to calculate an area dose. In the NDD method, doses are measured in advance, and a dose information table indicating a relationship between imaging conditions, such as a tube voltage and a tube current, and doses is generated. Then, a dose (incident surface dose) is obtained from the dose information table based on imaging information at the time of actual irradiation of an object with radiation and a distance between a radiation generating source and the object (SOD (Source-to-Object Distance)). Furthermore, according to Japanese Patent No. 4387644, in obtaining an area dose, an object region is extracted to calculate a dose of irradiation of an object from an irradiation dose per unit area.

However, obtainment of an area dose without using a dosimeter is not suggested in imaging in which a composite image (long-length image) is obtained from a plurality of radiographic images that are obtained through single radiation irradiation using a plurality of radiation detecting apparatuses as described in Japanese Patent No. 4708559.

SUMMARY OF THE INVENTION

The present invention provides a technique to enable the obtainment of an area dose without using an area dose meter in radiographic imaging that uses a plurality of radiation detecting apparatuses for obtaining a composite image.

According to one aspect of the present invention, there is provided a radiographic apparatus, comprising: a generating unit configured to generate a composite image using a plurality of radiographic images that have been obtained by a plurality of radiation detecting apparatuses through single radiation irradiation by a radiation generating unit; a determining unit configured to determine a region to be analyzed so as to eliminate an overlap in an overlapping portion arising from a spatial placement of the plurality of radiation detecting apparatuses; and an obtaining unit configured to obtain an area dose for the composite image by obtaining an area dose for the region to be analyzed determined by the determining unit.

According to another aspect of the present invention, there is provided an area dose obtaining apparatus that obtains an area dose in radiographic imaging in which a plurality of radiographic images are obtained through single radiation irradiation using a plurality of radiation detecting apparatuses for a purpose of generating a composite image, the apparatus comprising: a determining unit configured to determine a region to be analyzed so as to eliminate an overlap in an overlapping portion arising from a spatial placement of the plurality of radiation detecting apparatuses; and an obtaining unit configured to obtain an area dose for the composite image by obtaining an area dose for the region to be analyzed determined by the determining unit.

According to another aspect of the present invention, there is provided an area dose obtaining method used by a radiographic apparatus, the method comprising: generating a composite image using a plurality of radiographic images that have been obtained by a plurality of radiation detecting apparatuses through single radiation irradiation by a radiation generating unit; determining a region to be analyzed so as to eliminate an overlap in an overlapping portion arising from a spatial placement of the plurality of radiation detecting apparatuses; and obtaining an area dose for the composite image by obtaining an area dose for the determined region to be analyzed.

According to another aspect of the present invention, there is provided an area dose obtaining method used by an area dose obtaining apparatus that obtains an area dose in radiographic imaging in which a plurality of radiographic images are obtained through single radiation irradiation using a plurality of radiation detecting apparatuses for a purpose of generating a composite image, the method comprising: determining a region to be analyzed so as to eliminate an overlap in an overlapping portion arising from a spatial placement of the plurality of radiation detecting apparatuses; and obtaining an area dose for the composite image by obtaining an area dose for the determined region to be analyzed.

Further features of the present invention will become apparent from the following description of exemplary embodiments with reference to the attached drawings.

BRIEF DESCRIPTION OF THE DRAWINGS

FIGS. 4A to 4C show area dose analysis regions according to a first embodiment.

FIG. 8 is a flowchart showing an operation of a radiographic apparatus according to a second embodiment.

FIGS. 9A to 9C show area dose analysis regions according to the second embodiment.

DESCRIPTION OF THE EMBODIMENTS

Embodiments of the present invention will be described below with reference to the attached drawings. Note that, in the following embodiments, the term radiation may encompass not only X-rays but also, for example, α-rays, β-rays, particle beams of γ-rays, cosmic rays, and the like.

First Embodiment

Figure 1:
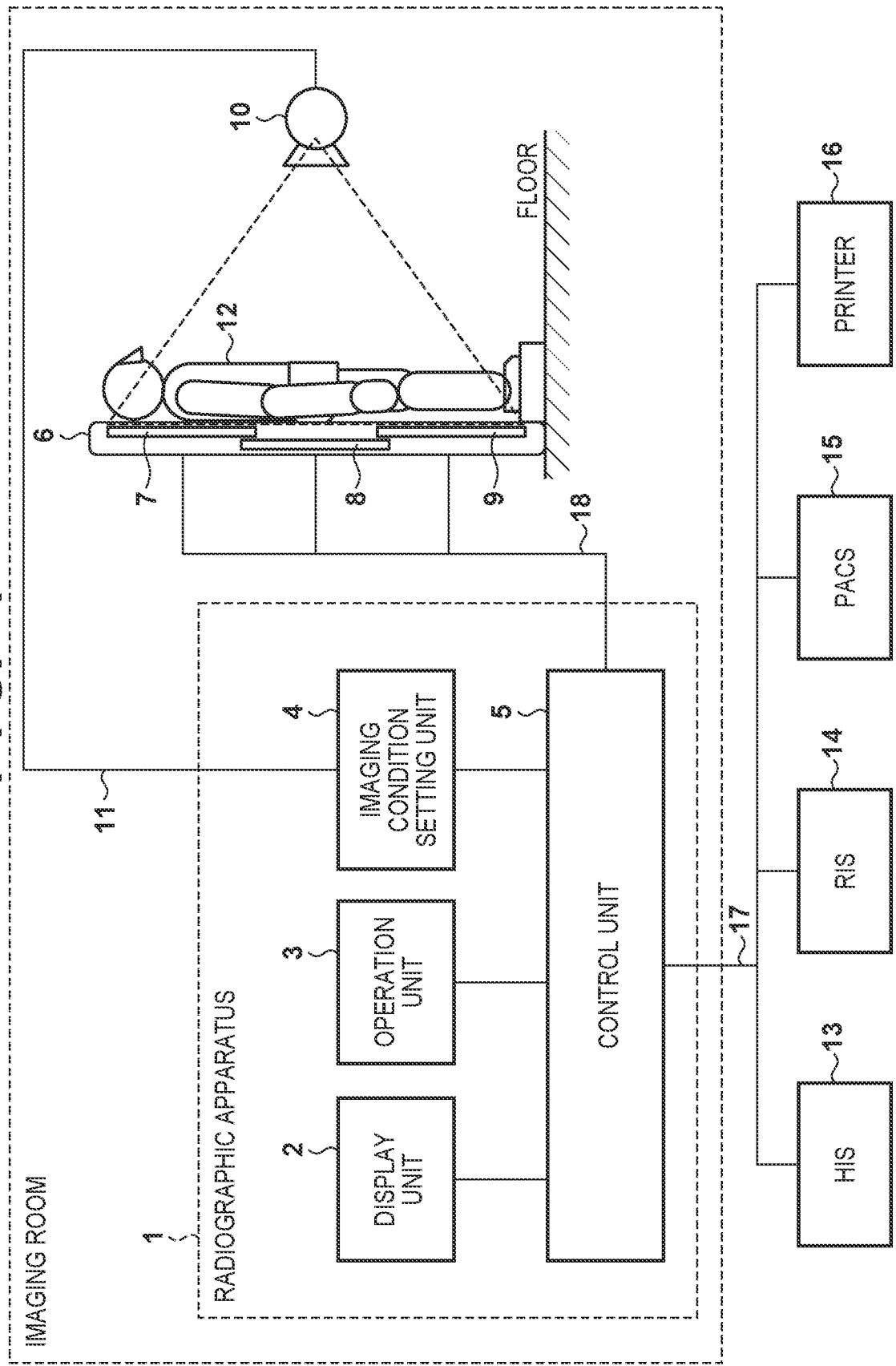
FIG. 1 is a block diagram showing an exemplary configuration of a radiographic system according to an embodiment.

A configuration of a radiographic system according to the first embodiment will now be described using FIG. 1. As shown in FIG. 1, a radiographic apparatus 1 in the radiographic system is connected to an HIS 13 that manages the progresses of examinations, and an RIS 14 that transmits examination orders to the radiographic apparatus 1. Note that HIS stands for Hospital Information System, and RIS stands for Radiology Information System. The radiographic apparatus 1 is also connected to a PACS 15 that manages radiographic images, and a printer 16 that outputs printouts of radiographic images. Note that PACS stands for Picture Archiving and Communication Systems.

The HIS 13 is a hospital management system, and includes a server that manages accounting information. When radiographic imaging is performed, an operator inputs a request for an examination from a terminal of the HIS 13. The input request is transmitted, as request information, from the HIS 13 to the RIS 14 of a radiography department of a hospital, which is a requested side. This request information is referred to as an examination order. An examination order includes a department name of a requesting side, examination items, personal data of an object, and the like.

The RIS 14 of the radiography department adds information related to radiographic imaging to the received examination order, and transmits them to the radiographic apparatus 1. Using the radiographic apparatus 1, an operator (e.g., a radiographer) performs radiographic imaging in accordance with the received examination order. The radiographic apparatus 1 adds examination information including the examination order to a radiographic image that has been obtained, and outputs them to the PACS 15 and the like. The PACS 15 is a server that is mainly aimed at the management of images. A task of inspecting the radiographic image, detailed post-processing, and a diagnosing task are performed using a high-definition monitor connected to the PACS 15. Also, information of the implementation of the examination by the radiographic apparatus 1 is transmitted to the HIS 13. The information of the implementation transmitted to the HIS 13 is used in the management of the progress of the examination, and also in accounting processing after the examination.

The radiographic apparatus 1, the HIS 13, the RIS 14, the PACS 15, and the printer 16 are connected via a network 17 constructed from, for example, a LAN (Local Area Network), a WAN (Wide Area Network), or the like. Note that each of these apparatuses includes one or more computers. The computer(s) includes, for example, a main control unit such as a CPU, and a storing unit such as a ROM (Read Only Memory) and a RAM (Random Access Memory). Furthermore, the computer(s) may include a communication unit such as a network card, input/output units such as a keyboard and a display or a touchscreen, and the like. Each of these units is connected via a bus or the like, and controlled by the main control unit executing programs stored in the storing unit.

As shown in FIG. 1, the radiographic apparatus 1 that performs radiographic imaging is installed in an imaging room. A radiation generating apparatus 10 that generates radiation, a plurality of radiation detecting apparatuses 7, 8, 9 that detect radiation that has passed through an object 12, and an imaging board 6 that supports the radiation detecting apparatuses 7, 8, 9 are also installed in the imaging room. The radiographic apparatus 1 includes a display unit 2 that displays a radiographic image, an operation unit 3 operated by an operator, an imaging condition setting unit 4 that sets imaging conditions (including a tube voltage, a tube current, and an irradiation period) on the radiation generating apparatus 10, and a control unit 5 that controls each constituent element.

The imaging condition setting unit 4 is connected to the radiation generating apparatus 10 via a cable 11. The imaging condition setting unit 4 sets imaging conditions (e.g., a tube voltage, a tube current, and an irradiation period) on the radiation generating apparatus 10. The radiation generating apparatus 10 functions as a radiation source that generates radiation, and operates under the imaging conditions set by the imaging condition setting unit 4. The radiation generating apparatus 10 is realized by, for example, a radiation tube, and irradiates the object 12 (e.g., a specific location on the object) with radiation. Note that the imaging condition setting unit 4 may obtain the imaging conditions for radiation irradiation executed by the radiation generating apparatus 10 from the radiation generating apparatus 10.

The radiation generating apparatus 10 can irradiate a desired irradiation range with radiation. The radiation generating apparatus 10 is installed via a supporting unit (not illustrated) mounted on a floor surface or a ceiling. Furthermore, a diaphragm (not illustrated) that shields radiation is mounted on an irradiation surface of the radiation generating apparatus 10. By controlling the diaphragm that shields radiation, the operator can set an irradiation range for radiation irradiation by the radiation generating apparatus 10.

The radiation detecting apparatuses 7, 8, 9 detect radiation from irradiation by the radiation generating apparatus 10 and passed through the object 12, and output image data corresponding to radiation (hereinafter referred to as radiographic images). More specifically, the radiation detecting apparatuses 7, 8, 9 detect radiation as charge that is equivalent to a radiation dose of radiation that has reached detection surfaces (including radiation that has passed through the object 12). For example, the radiation detecting apparatuses 7, 8, 9 use a sensor of a direct conversion type that directly converts radiation into charge, such as a-Se that converts radiation into charge, or a sensor of an indirect type that uses a scintillator such as CsI and a photoelectric converter such as a-Si. Furthermore, the radiation detecting apparatuses 7, 8, 9 generate radiographic images by applying A/D conversion to the detected charge, and output the radiographic images to the control unit 5. The radiation detecting apparatuses 7, 8, 9 may be of a cassette type in which the sensor is housed in a housing so that imaging can be performed with the sensor removed from the imaging board 6, or the sensor may be housed directly in the imaging board 6.

As shown in FIG. 1, the imaging board 6 is installed in such a manner that its longitudinal direction matches the vertical direction, that is, so as to stand upright with respect to the floor surface. Note that the imaging board 6 may be installed in such a manner that the longitudinal direction of the imaging board 6 matches the horizontal direction, that is, in such a manner that the longitudinal direction of the imaging board 6 is parallel to the floor surface. The imaging board 6 has a supporting function of supporting the object 12. The object 12 is positioned along the longitudinal direction of the imaging board 6.

In the imaging board 6, a plurality of radiation detecting apparatuses (in the example of FIG. 1, the radiation detecting apparatuses 7, 8, 9) are placed along the longitudinal direction of the imaging board 6. Here, the plurality of radiation detecting apparatuses are placed in such a manner that the radiation detecting apparatuses partially overlap one another. For example, as shown in FIG. 1, the radiation detecting apparatus 7 and the radiation detecting apparatus 8 are placed in such a manner that they partially spatially overlap each other, and imageable regions of the radiation detecting apparatus 7 and the radiation detecting apparatus 8 partially overlap each other. Similarly, the radiation detecting apparatus 8 and the radiation detecting apparatus 9 are placed in such a manner that they partially spatially overlap each other, and imageable regions of the radiation detecting apparatus 8 and the radiation detecting apparatus 9 partially overlap each other. Furthermore, the radiation detecting apparatus 8 is placed on the back side of the radiation detecting apparatus 7 and the radiation detecting apparatus 9 (in a position far from the radiation generating apparatus 10). Note that the placement of the radiation detecting apparatuses 7, 8, 9 is not limited to this. For example, the radiation detecting apparatus 8 may be placed on the back side of the radiation detecting apparatus 7 and the radiation detecting apparatus 9 may be placed on the back side of the radiation detecting apparatus 8, that is, the radiation detecting apparatuses 7, 8, 9 may be placed so that the distances between the radiation detecting apparatuses 7, 8, 9 and the radiation generating apparatus 10 increase in this order. Alternatively, for example, the radiation detecting apparatus 7 may be placed on the back side of the radiation detecting apparatus 8 and the radiation detecting apparatus 8 may be placed on the back side of the radiation detecting apparatus 9, that is, the radiation detecting apparatuses 9, 8, 7 may be placed so that the distances between themselves and the radiation generating apparatus 10 increase in this order.

Furthermore, in the present embodiment, the radiation generating apparatus 10 is installed in such manner that radiation is incident perpendicularly on the center of the radiation detecting apparatus 8. It goes without saying that the positional relationship between the radiation detecting apparatuses and the radiation generating unit is not limited to this. The object 12 can be imaged lengthwise by being imaged using the plurality of radiation detecting apparatuses through single radiation irradiation by the radiation generating apparatus 10. Radiation from irradiation directed to the plurality of radiation detecting apparatuses 7, 8, 9 by the radiation generating apparatus 10 passes through the object 12, and reaches and is simultaneously detected by the plurality of radiation detecting apparatuses 7, 8, 9.

The operation unit 3 operates processing in the radiographic apparatus 1. The display unit 2 is realized by, for example, a liquid crystal display or the like, and displays various types of information for the operator (an imaging technologist or a doctor). The operation unit 3 is constructed from, for example, a mouse, operation buttons, and the like, and inputs various types of instructions from the operator to each constituent element. Note that the display unit 2 and the operation unit 3 may be integrally realized as a touchscreen.

The control unit 5 of the radiographic apparatus 1 is connected to the plurality of radiation detecting apparatuses 7, 8, 9 via a cable 18. A power source, radiographic images, control signals, and the like are exchanged between the control unit 5 and the plurality of radiation detecting apparatuses 7, 8, 9 via the cable 18. The radiation detecting apparatuses 7, 8, 9 detect radiation that has passed through the object 12, and obtain a plurality of radiographic images based on the object. That is, imaging is performed by the radiation generating apparatus 10 and the plurality of radiation detecting apparatuses 7, 8, 9 operating in coordination with one another.

The radiographic apparatus 1 receives one or more examination orders for radiographic imaging from the RIS 14. An examination order includes, for example, object information and one or more imaging locations on the object. The control unit 5 issues an instruction to start radiographic imaging corresponding to at least one of the received examination orders. Here, the starting instruction is issued by, for example, the operator operating the operation unit 3. Alternatively, the control unit 5 may select an examination order for which imaging should be performed, and issue an instruction to start imaging.

In response to the instruction to start imaging, information indicating that radiographic imaging related to the aforementioned examination orders has been started is transmitted to the HIS 13. Accordingly, the HIS 13 changes the status of the aforementioned examination orders to the status indicating that the examination has been started. Thereafter, when every radiographic imaging corresponding to the aforementioned examination orders has been finished and the operator has input a confirmation of the completion of the examination orders via the operation unit 3, the control unit 5 transmits information indicating that the examination related to the examination orders has been finished to the HIS 13. Accordingly, the HIS 13 changes the status of the aforementioned orders to the status indicating that the examination has been finished.

Figure 2:
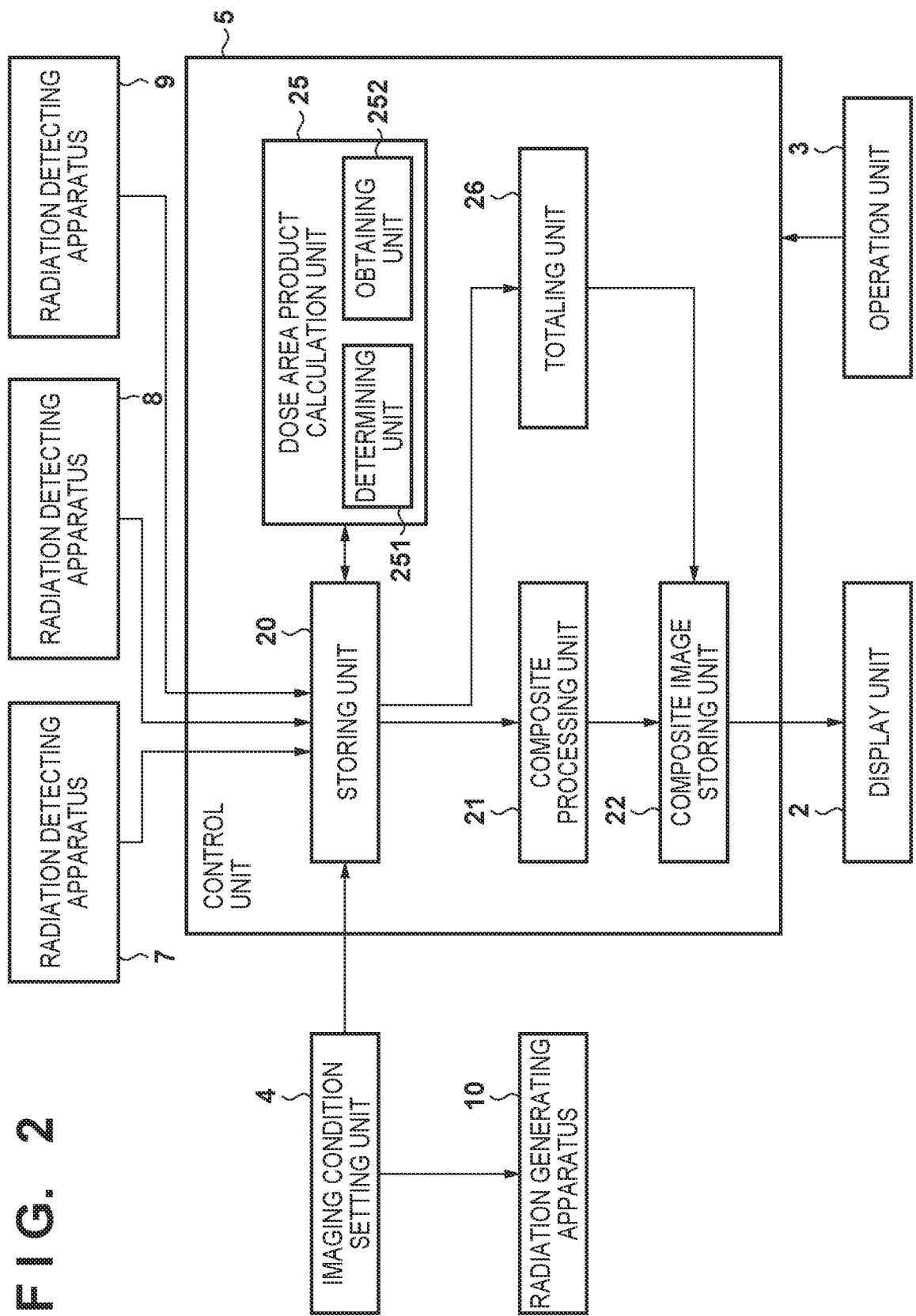
FIG. 2 is a block diagram showing an exemplary functional configuration of a control unit of a radiographic apparatus according to an embodiment.

Next, a description is given of processing executed by the control unit 5 of the radiographic apparatus 1 for obtaining an area dose for a composite image. FIG. 2 is a block diagram showing an exemplary functional configuration of the control unit 5 according to an embodiment. A storing unit 20 stores a plurality of radiographic images received from the radiation detecting apparatuses 7, 8, 9. A composite processing unit 21 generates a composite image (long-length image) using the plurality of radiographic images that have been obtained by the plurality of radiation detecting apparatuses through single radiation irradiation by the radiation generating unit and stores the composite image in a composite image storing unit 22. A dose area product calculation unit 25 obtains an incident dose based on the imaging conditions set on the radiation generating apparatus 10 using, for example, an NDD method, and obtains area doses respectively for the plurality of radiographic images using the obtained incident dose. The obtained area doses are stored in the storing unit 20. A totaling unit 26 calculates a total area dose, which is a total of the plurality of area doses that have been obtained by the dose area product calculation unit 25 and stored in the storing unit 20, and stores the total area dose in a composite image storing unit 22 as an area dose for the composite image generated by the composite processing unit 21. The composite image storing unit 22 stores the composite image and the area dose for the composite image in association with each other. Note that, although the storing unit 20 and the composite image storing unit 22 are described in distinction from each other in the present embodiment, the storing unit 20 and the composite image storing unit 22 may be constructed from a shared storing unit (one storing unit).

The control unit 5 is connected to the radiation detecting apparatuses 7, 8, 9 via, for example, a wired or wireless network or a dedicated line. FIG. 1 shows an exemplary configuration in which they are connected via the cable 18. The radiation detecting apparatuses 7, 8, 9 image radiation from irradiation by the radiation generating apparatus 10, and output the obtained radiographic images to the control unit 5. The control unit 5 has an application function that operates on a computer. The control unit 5 controls the operations of the radiation detecting apparatuses 7, 8, 9, and output the radiographic images and graphical user interfaces to the display unit 2.

The imaging condition setting unit 4 sets imaging conditions (including a tube voltage, a tube current, and an irradiation period) on the radiation generating apparatus 10. The control unit 5 controls the timing at which the radiation generating apparatus 10 performs radiation irradiation, and the timing at which the radiation detecting apparatuses 7, 8, 9 execute imaging. More specifically, the control unit 5 causes the radiation generating apparatus 10 to perform single radiation irradiation, and the radiation detecting apparatuses 7, 8, 9 perform imaging simultaneously in accordance with the irradiation by the radiation generating apparatus 10. That is, the control unit 5 causes the radiation detecting apparatuses 7, 8, 9 to perform imaging simultaneously, and causes the radiation detecting apparatuses 7, 8, 9 to output the plurality of radiographic images.

Note that the control unit 5 may apply image processing such as noise removal to the radiographic images output from the radiation detecting apparatuses 7, 8, 9, and store the resultant radiographic images in the storing unit 20. Furthermore, the control unit 5 may be configured so that it can apply image processing such as trimming and rotation to the radiographic images output from the radiation detecting apparatuses 7, 8, 9. The display unit 2 displays the radiographic images output from the control unit 5.

As stated earlier, the object 12 stands on a step mounted on the imaging board 6, and is positioned relative to the radiation detecting apparatuses 7, 8, 9 and the radiation generating apparatus 10. Radiation from irradiation directed to the radiation detecting apparatuses 7, 8, 9 by the radiation generating apparatus 10 passes through the object 12, and reaches and is detected by the radiation detecting apparatuses 7, 8, 9. The control unit 5 applies composite processing to the plurality of radiographic images obtained by the radiation detecting apparatuses 7, 8, 9, thereby generating a composite image of the object 12. The composite image is a long-length image obtained through lengthwise imaging that has a wide observation region. The display unit 2 displays the composite image output from the control unit 5. In this way, the radiographic system according to the present embodiment can perform lengthwise imaging, which images the spinal cord, the entire legs, and the entire body of the object 12, through single radiation irradiation.

Note that, although the control unit 5 controls the timing of imaging by the radiation detecting apparatuses 7, 8, 9 in the above description, no limitation is intended by this. For example, the radiation detecting apparatuses 7, 8, 9 may have a detection function of automatically detecting the radiation irradiation by the radiation generating apparatus 10. The detection function is a function whereby, when the radiation generating apparatus 10 performs the radiation irradiation, the radiation detecting apparatuses 7, 8, 9 detect the radiation and accumulate charge attributed to the radiation.

Also, the storing unit 20 stores the radiographic images output from the radiation detecting apparatuses 7, 8, 9 together with the imaging conditions set by the imaging condition setting unit 4. That is, in storing the plurality of radiographic images in the storing unit 20, these plurality of radiographic images are stored in the storing unit 20 with the imaging conditions appended thereto. Furthermore, the storing unit 20 stores the radiographic images output from the radiation detecting apparatuses 7, 8, 9 together with time information. This time information makes it possible to distinguish whether the radiographic images that have been output from the radiation detecting apparatuses 7, 8, 9 and stored in the storing unit 20 were obtained simultaneously. Furthermore, the storing unit 20 stores the plurality of radiographic images obtained by the radiation detecting apparatuses 7, 8, 9 in association with position information (spatial placement information) of the radiation detecting apparatuses 7, 8, 9. The storing unit 20 can output the plurality of radiographic images and their position information to the composite processing unit 21 and the dose area product calculation unit 25.

The composite processing unit 21 generates a composite image (long-length image) by compositing the plurality of radiographic images stored in the storing unit 20. Specifically, the composite processing unit 21 generates the composite image by compositing the plurality of radiographic images that have been respectively output from the radiation detecting apparatuses 7, 8, 9 based on their respective position information. The composite processing unit 21 determines a positional relationship between the plurality of radiographic images that have been respectively output from the radiation detecting apparatuses 7, 8, 9 (e.g., a top part, a middle part, and a bottom part) based on the position information, and composites the respective radiographic images so that they partially overlap one another. In this way, the composite processing unit 21 generates the composite image (long-length image) by compositing the plurality of radiographic images. The composite processing unit 21 can also apply image processing such as tone processing to the composite image. The composite image storing unit 22 stores the composite image obtained by the composite processing unit 21, that is, the long-length image.

The dose area product calculation unit 25 has a determining unit 251 and an obtaining unit 252, and calculates area doses based on the radiographic images and their imaging conditions stored in the storing unit 20. Note that the dose area product calculation unit 25 may be connected to the radiation detecting apparatuses 7, 8, 9, and obtain area doses using the radiographic images that are respectively output from the radiation detecting apparatuses 7, 8, 9. The dose area product calculation unit 25 calculates area doses respectively for the plurality of radiographic images obtained by the radiation detecting apparatuses 7, 8, 9. An area dose is, for example, a Dose-Area Product (DAP). An area dose is a value that indicates a dose used in radiographic imaging. Below is a specific description of area dose calculation processing by the dose area product calculation unit 25.

Figure 3:
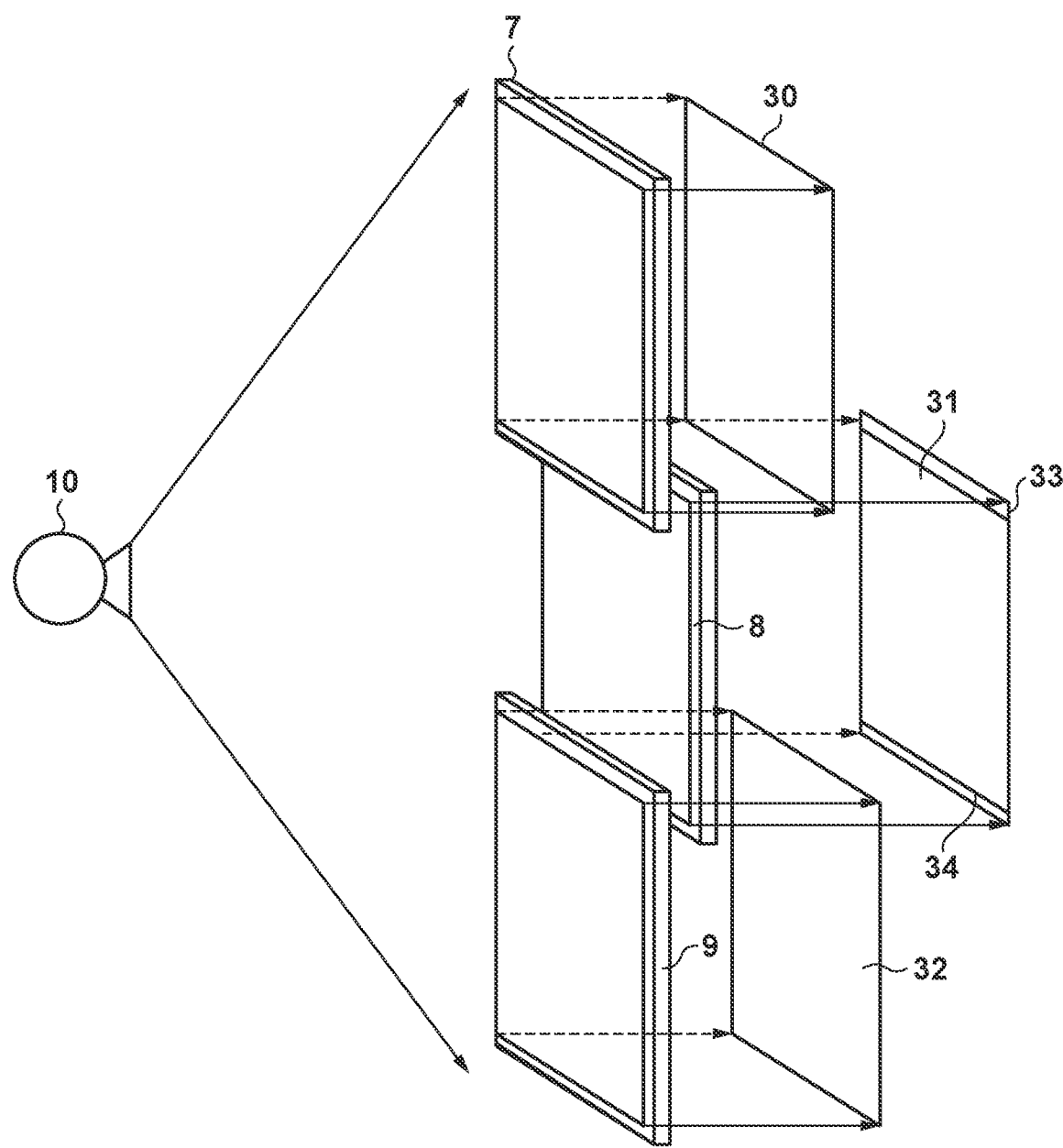
FIG. 3 shows the placement of radiation detecting apparatuses and regions excluded from area dose analysis according to an embodiment.

First, the determining unit 251 of the dose area product calculation unit 25 determines the area of regions to be analyzed, with removal of overlapping portions arising from the spatial placement of the plurality of radiation detecting apparatuses. The overlapping portions are extracted based on the position information of the plurality of radiation detecting apparatuses. In the first embodiment, the determining unit 251 sets the regions to be analyzed (hereinafter referred to as analysis regions) respectively in the plurality of radiographic images, and calculates the area of the analysis regions. FIG. 3 is a diagram for describing spatial overlapping of imageable regions of the radiation detecting apparatuses. To calculate the area of the analysis regions, the determining unit 251 excludes, from the analysis regions, regions 33, 34 of the overlapping portions where the imageable regions of the radiation detecting apparatuses 7, 8, 9 that obtained radiographic images 30, 31, 32 spatially overlap one another. The regions 33, 34 of the overlapping portions can be extracted based on the position information of the radiation detecting apparatuses 7 to 9.

FIGS. 4A to 4C are diagrams for describing examples of the analysis regions that are determined in the radiographic images by the determining unit 251. FIG. 4A shows an example in which regions obtained by removing the overlapping portions from the entirety of the radiographic images are used as the analysis regions. In this case, the determining unit 251 sets the entire regions with removal of the region 33 and the region 34, that is, the regions indicated by bold frames 40 to 42, as the analysis regions of the radiographic images 30 to 32. Also, the analysis regions may be the regions where radiation irradiation exists in the radiographic images, and this example is shown in FIG. 4B. In this case, the determining unit 251 sets the portions indicated by bold frames 43 to 45 as the analysis regions of the radiographic images 30 to 32. The bold frames 43 to 45 surround the regions where radiation irradiation exists. The bold frames 43 to 45 can be set from collimator information obtained from the radiation generating apparatus 10, image analysis information obtained by analyzing the radiographic images 30 to 32, or the like. Note that the bold frame 44 is set with removal of the region 33 and the region 34. Also, the analysis regions may be the regions of the object in the radiographic images, and this example is shown in FIG. 4C. In this case, the determining unit 251 sets the regions indicated by bold frames 46 to 48 as the analysis regions of the radiographic images 30 to 32. The bold frames 46 to 48 indicate a boundary between the object and the exterior of the object. The regions of the object can be obtained by analyzing the radiographic images 30 to 32. In FIG. 4C also, the region 33 and the region 34, in which the imaging regions of the radiation detecting apparatuses spatially overlap one another, are excluded from the regions to be analyzed, similarly to FIGS. 4A and 4B. Note that, in the examples shown in FIGS. 4A to 4C, the regions 33, 34 of the overlapping portions are excluded from the analysis target with respect to the radiographic image 31 obtained by the radiation detecting apparatus 8. This is because the radiation detecting apparatuses 7 to 9 are placed as shown in FIG. 3. Regions to be excluded from the analysis target, as well as a radiographic image in which the regions are to be excluded, are determined in accordance with the placement of the plurality of radiation detecting apparatuses.

Using, for example, the NDD method, the obtaining unit 252 of the dose area product calculation unit 25 obtains a dose at a detection position based on the imaging conditions set by the imaging condition setting unit 4 and a distance between the detection position and the radiation generating apparatus 10. For example, provided that a dose detection position is the object, an SOD (Source-to-Object Distance) representing a distance between the radiation generating unit and the object can be used as a distance between the detection position and the radiation generating apparatus 10. Then, the obtaining unit 252 calculates an area dose (DAP) based on the area of the analysis regions obtained through the analysis of the radiographic images and the dose obtained at the detection position. For example, the area dose is calculated by multiplying the obtained dose by the area of the analysis regions.

Figure 10:
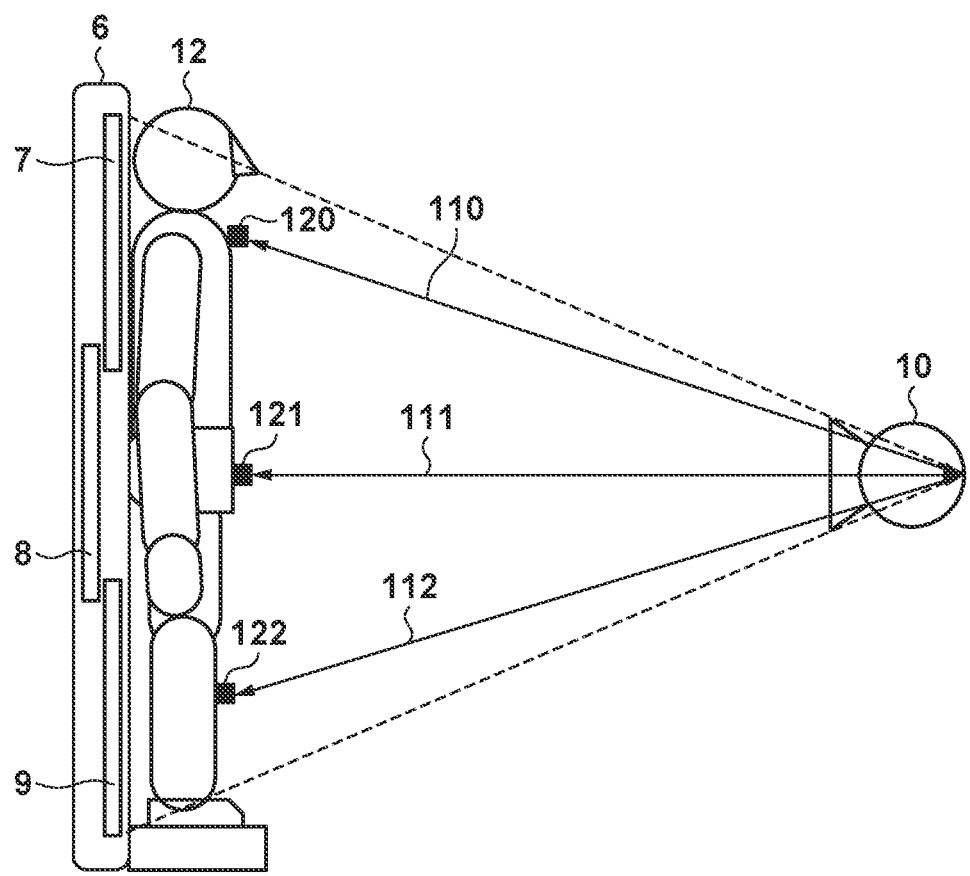
FIG. 10 is a diagram for describing dose detection positions.

The obtaining unit 252 may set SODs of different values respectively for the plurality of radiographic images, or may set SODs of the same value for the plurality of radiographic images. FIG. 10 shows examples of distances (SODs) between the radiation generating apparatus 10 (focal spot) and the object 12, which are used in dose conversion. Detection positions 120 to 122 are dose detection positions corresponding to the radiation detecting apparatuses 7 to 9, and distances 110 to 112 from the radiation generating apparatus 10 and the detection positions 120 to 122 represent SODs. The obtaining unit 252 may obtain a dose that corresponds to the plurality of radiographic images using a dose at a shared detection position (e.g., the detection position 121) with respect to the plurality of radiation detecting apparatuses. Alternatively, the obtaining unit 252 may obtain doses that respectively correspond to the plurality of radiographic images based on the distances 110 to 112 from the radiation generating apparatus 10 to the detection positions 120 to 122 that respectively correspond to the plurality of radiation detecting apparatuses. The obtaining unit 252 calculates an area dose for the composite image based on the doses obtained at the detection positions and the area of the analysis target determined by the determining unit 251.

Note that the dose detection positions may be located on detection surfaces of the radiation detecting apparatuses. Also, an SOD that has been set with respect to one of the plurality of radiation detecting apparatuses and the position information of the plurality of radiation detecting apparatuses may be used as the basis for determining the SODs corresponding to other radiation detecting apparatuses. That is, the SODs may be determined respectively for the radiographic images obtained by the radiation detecting apparatuses 8, 9 from the SOD determined for the radiographic image obtained by the radiation detecting apparatus 7 based on the position information indicating the spatial placement of the plurality of radiation detecting apparatuses. Similarly, the SODs may be determined respectively for the radiographic images obtained by the radiation detecting apparatuses 7, 9 from the SOD determined for the radiographic image obtained by the radiation detecting apparatus 8 based on the position information. Also, the SODs may be determined respectively for the radiographic images obtained by the radiation detecting apparatuses 7, 8 from the SOD determined for the radiographic image obtained by the radiation detecting apparatus 9 based on the position information. Furthermore, although the dose area product calculation unit 25 calculates DAPs as area doses, area doses other than DAPs may be used as long as the values of the doses that have reached the radiation detecting apparatuses 7, 8, 9 can be determined using the area doses.

The area doses for the plurality of radiographic images that have been calculated by the dose area product calculation unit 25 in the above-described manner are stored in the storing unit 20 together with the radiographic images and the imaging conditions. That is, the storing unit 20 stores the radiographic images output from the radiation detecting apparatuses 7, 8, 9 together with the imaging conditions of the radiation generating apparatus 10 set by the imaging condition setting unit 4 and the area doses calculated by the dose area product calculation unit 25.

The totaling unit 26 obtains an area dose for the composite image (long-length image) by totaling the plurality of area doses that have been obtained by the dose area product calculation unit 25 with respect to the plurality of radiographic images. When the composite image is an image obtained by compositing two radiographic images, the totaling unit 26 totals two area doses for the two radiographic images that compose the composite image. When the composite image is an image obtained by compositing three radiographic images, the totaling unit 26 totals three area doses for the three radiographic images that compose the composite image. As described above, due to the coordinated operations of the obtaining unit 252 and the totaling unit 26, the area dose for the composite image is obtained by obtaining the area doses with respect to the regions to be analyzed, which have been determined by the determining unit 251 and from which the overlapping portions have been excluded. In the above-described example, the area dose for the composite image is obtained based on the doses at the detection positions, which are obtained based on the imaging conditions for single radiation irradiation and the distances between the radiation generating unit and the detection positions, and the determined area of the analysis target.

Figure 5:
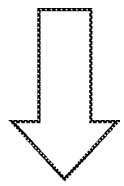
FIG. 5 shows the result of obtaining area doses (Dose Area Products or DAPs) according to the first embodiment.

FIG. 5 is a diagram for describing the calculation of area doses by the totaling unit 26. A table 5a of FIG. 5 shows area doses and imaging conditions for the plurality of radiographic images that have been obtained by the dose area product calculation unit 25 and stored in the storing unit 20. A table 5b shows the stored result of calculation, by the totaling unit 26, of an area dose for the composite image from the plurality of area doses. It is assumed here that the composite image has been generated by obtaining three radiographic images. As shown in the table 5a, image IDs (001 to 003) are respectively added to the radiographic images. The area doses (DAPs) calculated by the dose area product calculation unit 25 are respectively recorded for the radiographic images. The imaging conditions (including a tube voltage, a tube current, and an irradiation period) of the radiation generating apparatus 10 may be appended only to one radiographic image, or may be appended to each radiographic image.

As shown in the table 5a, regarding an image (ID=001) corresponding to the radiographic image that was received first, the area dose (DAP) is 105, the tube voltage is V1, the tube current is I1, and the irradiation period is T1. Regarding an image (ID=002) corresponding to the radiographic image that was received second, the area dose (DAP) is 110. Regarding an image (ID=003) corresponding to the radiographic image that was received third, the area dose (DAP) is 100. In this manner, the storing unit 20 stores the radiographic images obtained through radiographic imaging, the area doses calculated by the dose area product calculation unit 25, and the imaging conditions of the radiation generating apparatus 10 in association with one another.

The totaling unit 26 totals the plurality of area doses that have been calculated by the dose area product calculation unit 25. As shown in the table 5b, the totaling unit 26 uses a total of the plurality of area doses that have been calculated by the dose area product calculation unit 25 as the area dose for the composite image. Specifically, the totaling unit 26 totals the area doses (DAPs) appended to the plurality of radiographic images. Here, the totaling unit 26 totals 105, 110, and 100, which are respectively the area dose (DAP) for the image of ID=001, the area dose (DAP) for the image of ID=002, and the area dose (DAP) for the image of ID=003. Then, the totaling unit 26 outputs 315, which is the total area dose (DAP), to the composite image storing unit 22 as the area dose for the composite image (ID=004). At this time, image information and imaging conditions (including a tube voltage, a tube current, and an irradiation period) for the radiographic images composing the composite image are output to the composite image storing unit 22.

The composite image storing unit 22 stores the composite image composited by the composite processing unit 21 together with the area dose (DAP=315) for the composite image. The composite image storing unit 22 can also store the composite image together with the image information of the radiographic images composing the composite image. The display unit 2 displays the composite image together with the image information of the radiographic images composing the composite image. Therefore, the operator can acknowledge the radiographic images from which the area doses have been totaled to yield the area dose for the composite image.

Furthermore, the composite image (long-length image) obtained by the radiographic apparatus 1 is transmitted to the PACS 15 (external apparatus) together with the area dose for the composite image. Also, the composite image may be transmitted to the PACS 15 together with the imaging conditions associated with the area dose for the composite image and the radiographic images composing the composite image. The high-definition monitor connected to the PACS 15 can display the composite image and the area dose for the composite image. Therefore, the operator can acknowledge the area dose for the composite image. Furthermore, the PACS 15 stores the area dose for the composite image obtained by the radiographic apparatus 1 together with the composite image. The PACS 15 can also calculate statistic values, such as a summed value and an average value of area doses, for the composite image on a per-object basis. In this manner, the operator can manage doses on the imaged object.

Furthermore, the composite image storing unit 22 can store the composite image together with the imaging conditions for the radiographic images composing the composite image. That is, the composite image storing unit 22 stores the imaging conditions (tube voltage V1, tube current I1, and irradiation period T1) for the image ID=001 together with the composite image. The display unit 2 displays the composite image together with the imaging conditions for the radiographic images composing the composite image. Therefore, the operator can acknowledge under what imaging conditions the area dose was used for the composite image.

Figure 6:
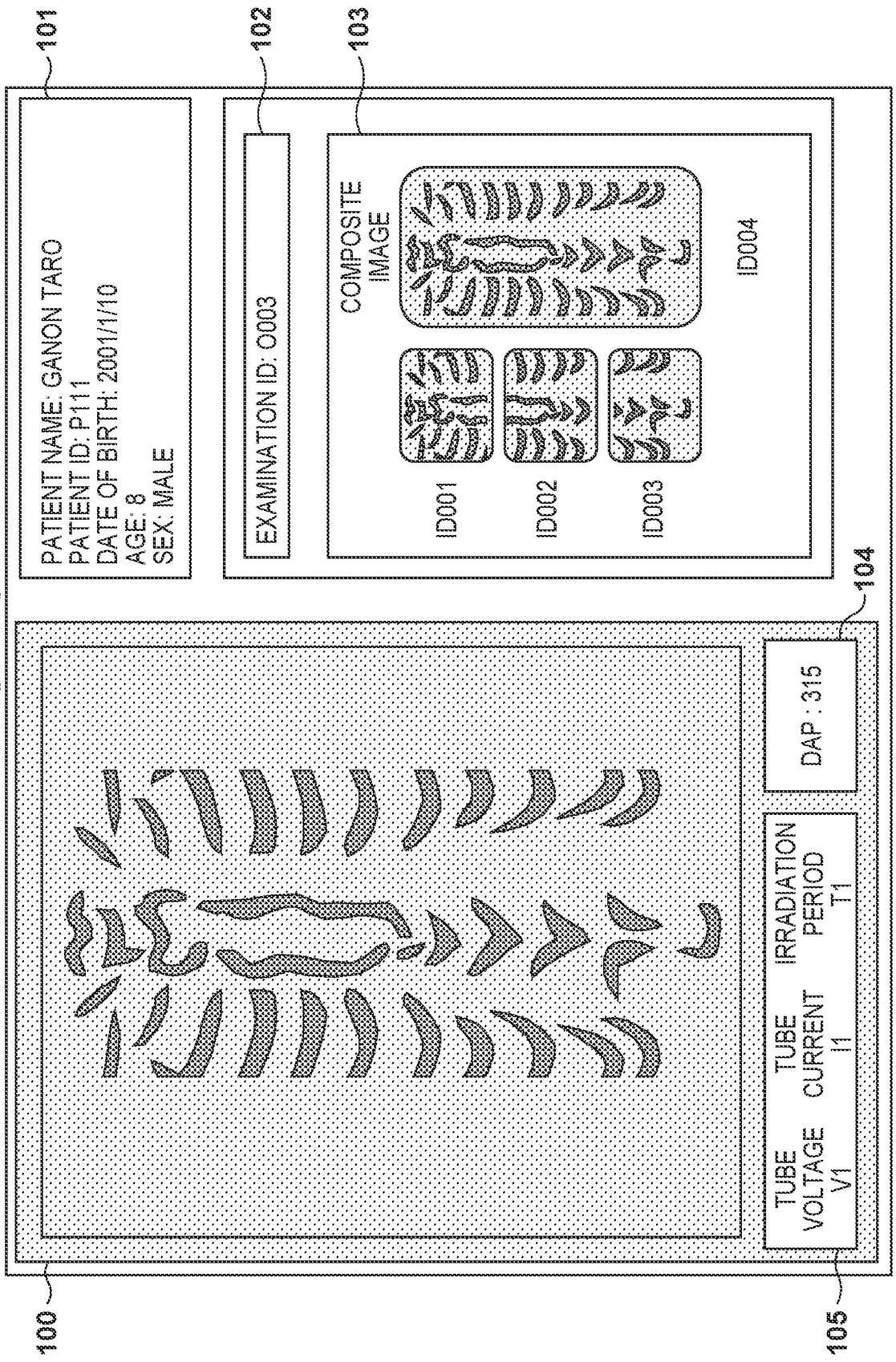
FIG. 6 shows exemplary display by a radiographic system according to an embodiment.

FIG. 6 shows a display mode of the display unit 2 in the radiographic system. The display unit 2 displays a composite image 100 composited by the composite processing unit 21.

As shown in FIG. 6, the display unit 2 displays the composite image 100 composited by the composite processing unit 21, object information 101, examination information 102, and a thumbnail image 103 for the composite image. The display unit 2 also displays an area dose 104 for the composite image, image information of the radiographic images composing the composite image, and imaging conditions 105 for these radiographic images. The display unit 2 displays at least the composite image 100 and the area dose 104 for the composite image on the same screen. Furthermore, it is preferable to display, simultaneously with the composite image 100, the imaging conditions 105 for the radiographic images using which the area dose for the composite image was calculated.

The object information 101 contains the name, ID, date of birth, age, sex, and the like of the object. The examination information 102 contains an examination ID. The area dose 104 (DAP: 315) and the imaging conditions 105 (tube voltage V1, tube current I1, and irradiation period T1) for the composite image are displayed on an edge of the composite image 100. The edge of the composite image 100 is a region that does not overlap a region of interest of an imaging location on the object. Therefore, the operator can acknowledge the extent of the area dose for the composite image 100. The operator can also acknowledge the extent of the imaging conditions for the composite image 100.

The display unit 2 displays information of the radiographic images composing the composite image in the vicinity of the thumbnail image 103 for the composite image. Therefore, the operator can acknowledge the radiographic images from which the area dose for the composite image has been calculated. Furthermore, at least one of area dose values in FIGS. 4A, 4B, and 4C can be displayed by settings. In addition, a plurality of area dose values may be displayed together with, for example, area dose values from the past, area dose values obtained using other methods (e.g., different analysis regions shown in FIGS. 4A to 4C), or the like. Note that the display unit 2 may display the area dose 104 and the imaging conditions 105 for the composite image in the vicinity of the thumbnail image 103 for the composite image.

Figure 7:
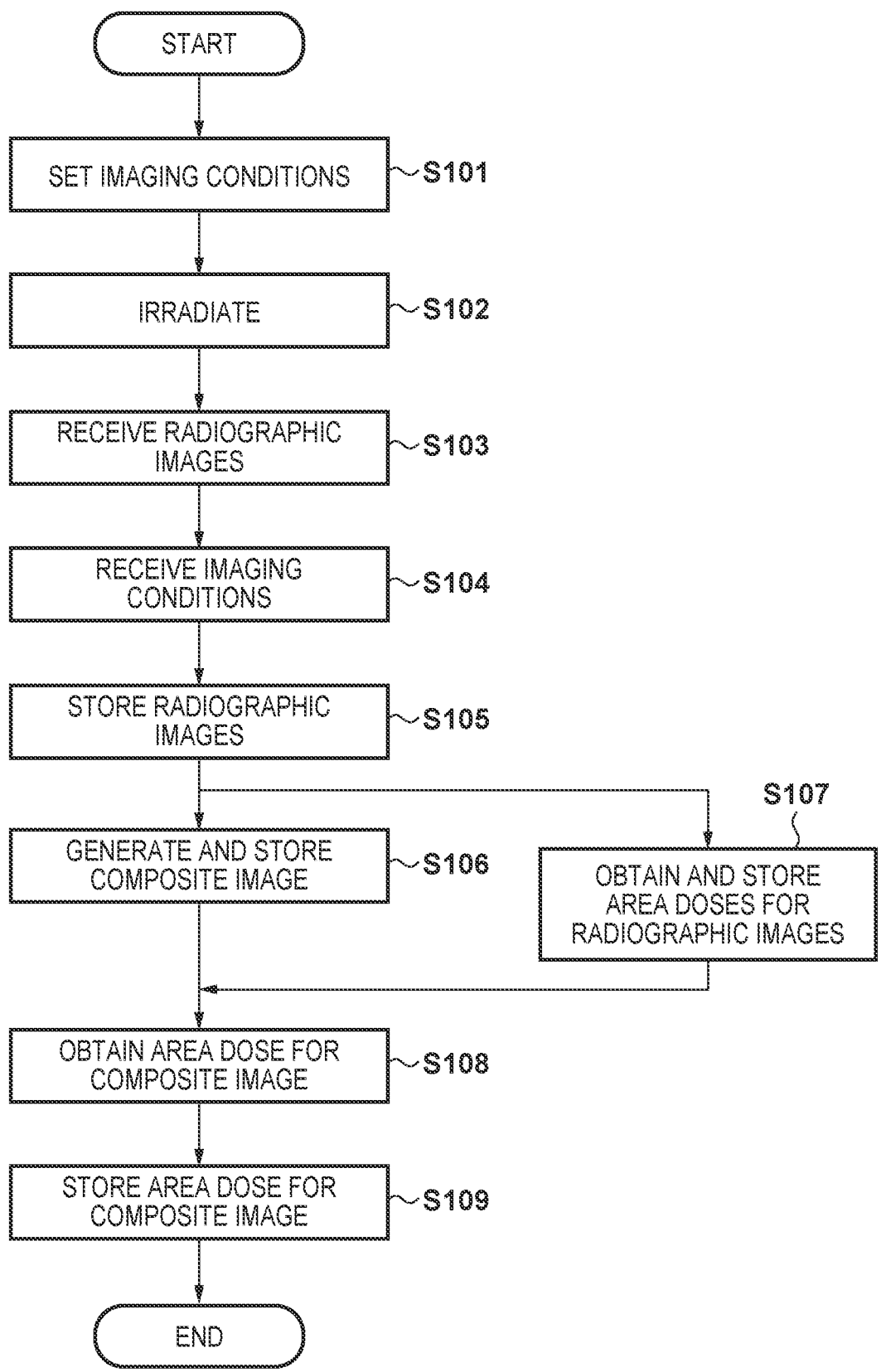
FIG. 7 is a flowchart showing an operation of a radiographic apparatus according to the first embodiment.

Next, the operation of the radiographic apparatus 1 will be described using a flowchart shown in FIG. 7.

First, the operator sets imaging conditions (including a tube voltage, a tube current, and an irradiation period) on the radiation generating apparatus 10 using the imaging condition setting unit 4. Upon accepting the settings of the imaging conditions by the operator, the imaging condition setting unit 4 sets the accepted imaging conditions on the radiation generating apparatus 10 (step S101). Next, the operator places the radiation detecting apparatuses 7, 8, 9 inside the imaging board 6, and positions the object 12 along the longitudinal direction of the imaging board 6. At this time, as has been described using FIG. 3, the plurality of radiation detecting apparatuses are placed in such a manner that the radiation detecting apparatuses partially overlap one another. When the operator issues an exposure instruction in this state, the radiation generating apparatus 10 performs single radiation irradiation under the imaging conditions set in step S101 (step S102).

The radiation directed to the radiation detecting apparatuses 7, 8, 9 through the single irradiation passes through the object 12, and reaches and is detected by the respective radiation detecting apparatuses 7, 8, 9. The radiation detecting apparatuses 7, 8, 9 respectively detect the radiation from the single irradiation by the radiation generating apparatus 10, and execute imaging. The control unit 5 causes the radiation detecting apparatuses 7, 8, 9 to respectively output radiographic images obtained through the imaging, and receives the radiographic images (step S103). The control unit 5 also receives the imaging conditions for the radiation that have been set on the radiation generating apparatus 10 from the imaging condition setting unit 4 (step S104). The control unit 5 stores the received plurality of radiographic images and imaging conditions in the storing unit 20 in association with each other (step S105). At this time, they are stored with distinction of the locations at which the radiographic images were obtained. Position information of the radiation detecting apparatuses may be stored in the storing unit 20. The composite processing unit 21 generates a composite image (long-length image) by compositing the plurality of radiographic images that were stored in the storing unit 20 in step S105 based on their position information, and stores the composite image in the composite image storing unit 22 (step S106).

On the other hand, the dose area product calculation unit 25 obtains area doses respectively for the plurality of radiographic images that were stored in the storing unit 20 in step S105, and stores the area doses in the storing unit 20 (step S107). The processes of steps S106 and S107 may be executed in parallel, or one of them may be executed prior to the other. The determining unit 251 and the obtaining unit 252 obtain the area doses in the above-described manner. As a result, for example, when three radiographic images have been obtained, the storing unit 20 stores the first radiographic image, the area dose obtained by the dose area product calculation unit 25 for the first radiographic image, and the imaging conditions of the radiation generating apparatus 10 at the time of obtaining of the first radiographic image in association with one another. Also, the storing unit 20 stores the second radiographic image and the area dose calculated by the dose area product calculation unit 25 for the second radiographic image in association with each other. Similarly, the storing unit 20 stores the third radiographic image and the area dose calculated by the dose area product calculation unit 25 for the third radiographic image in association with each other.

The totaling unit 26 calculates an area dose for the composite image from the plurality of area doses obtained in step S107 (step S108). More specifically, the totaling unit 26 calculates an area dose for the composite image from the plurality of area doses for the plurality of radiographic images that compose the composite image (long-length image) generated by the composite processing unit 21. Subsequently, the totaling unit 26 stores the area dose for the composite image calculated in step S108 in the composite image storing unit 22, in association with the composite image stored in step S106 (step S109).

As described above, in the radiographic system according to the first embodiment, the area of regions to be analyzed is determined with removal of overlapping portions arising from the spatial placement of the plurality of radiation detecting apparatuses. Then, the area dose for the composite image is obtained based on the doses at the detection positions, which are obtained based on the imaging conditions for single radiation irradiation and the distances between the radiation generating unit and the detection positions, and the determined area of regions to be analyzed. In this way, the area dose for the composite image can be obtained without installing an area dose meter, and dose management can be performed with respect to the composite image.

Second Embodiment

In the first embodiment, an area dose for a composite image (long-length image) is obtained by totaling area doses that have been obtained with respect to analysis regions from which overlapping portions of radiographic images, which have been obtained from the discrete radiation detecting apparatuses, have been excluded. In the second embodiment, an area dose is obtained with respect to an analysis region that has been determined for a composite image (long-length image). That is, overlapping portions are removed from the analysis region as the determining unit 251 determines the area of the analysis target with respect to the composite image. Note that configurations according to the second embodiment are similar to those according to the first embodiment (FIGS. 1 to 3). However, it is assumed that the composite processing unit 21 and the dose area product calculation unit 25 are connected in FIG. 2. FIG. 8 is a flowchart showing an operation of the radiographic system according to the second embodiment. Below, the operation of the radiographic system according to the second embodiment will be described using a flowchart shown in FIG. 8. Note that processing shown in FIG. 8 is processing that is to replace steps S108 and S109 of FIG. 7.

The operator sets, via the operation unit 3, whether to use a composite image as a target of area dose calculation. The control unit 5 determines whether the calculation of an area dose for the composite image has been set as a target of area dose calculation (step S201). If the calculation of an area dose for the composite image has been set as a target of area dose calculation, the processing proceeds to step S202. On the other hand, if the setting is such that the calculation of an area dose for the composite image is not to be performed as a target of area dose calculation, the processing proceeds to step S203.

When the calculation of an area dose for the composite image is not to be performed as a target of area dose calculation, the totaling unit 26 calculates an area dose for the composite image by totaling a plurality of area doses that have been obtained for a plurality of radiographic images composing the composite image (step S203). This process is similar to step S108 of the first embodiment (FIG. 7). When the area doses have been obtained as shown in the table 5a (FIG. 5), the totaling unit 26 totals 105, 110, and 100, which are respectively the area dose for the image of ID 001, the area dose for the image of ID=002, and the area dose for the image of ID=003. The totaling unit 26 stores the calculated area dose for the composite image in the composite image storing unit 22 in association with the corresponding composite image (step S204).

On the other hand, when the calculation of an area dose for the composite image is to be performed as a target of area dose calculation, the dose area product calculation unit 25 calculates an area dose that represents an incident area dose on the radiation detecting apparatuses 7, 8, 9 from the composite image (step S202). The area dose is, for example, a DAP. The determining unit 251 of the dose area product calculation unit 25 sets an analysis region in the composite image (long-length image) generated by the composite processing unit 21, and calculates the area of the analysis region. FIGS. 9A to 9C are diagrams for describing a range that is set by the dose area product calculation unit 25 as the analysis region. FIG. 9A shows an exemplary case in which the entire composite image is used as the analysis region. In this case, the determining unit 251 sets the entirety of a composite image 901 indicated by a bold frame 50 as the analysis region. FIG. 9B shows an example in which a region where radiation irradiation exists in the composite image is used as the analysis region. In this case, the determining unit 251 sets a portion indicated by a bold frame 51, which has been irradiated with radiation in the composite image 901, as the analysis region. Furthermore, FIG. 9C shows an example in which a region of an object in the composite image is used as the analysis region. In this case, the determining unit 251 sets an object portion inside the composite image 901 as indicated by a bold frame 52.

The obtaining unit 252 of the dose area product calculation unit 25 obtains an area dose based on the area of the analysis region set in the above-described manner, imaging conditions set by the imaging condition setting unit 4, and a relationship between a known SOD and an incident surface dose. The composite processing unit 21 stores the area dose for the composite image in the composite image storing unit 22 in association with the corresponding composite image. By using the composite image 901, the region 33 and the region 34 shown in FIG. 3 are excluded from the region to be analyzed.

The composite image storing unit 22 stores the composite image (long-length image) composited by the composite processing unit 21 together with the area dose for the composite image. That is, the area dose for the composite image calculated in step S202 is stored in the composite image storing unit 22 as an appendix to the composite image.

As described above, according to the second embodiment, the area dose for the composite image is obtained without using an area dose meter by calculating the area dose for the analysis region determined from the composite image (long-length image).

As described above, according to each of the foregoing embodiments, the area dose for the composite image (long-length image), which is a composite of a plurality of radiographic images obtained by performing single radiation irradiation directed to the plurality of radiation detecting apparatuses, can be obtained without using an area dose meter. In this way, dose management can be performed with respect to the composite image.

Note that, although the radiographic apparatus 1, which generates the composite image by obtaining the plurality of radiographic images, obtains area doses in each of the foregoing embodiments, no limitation is intended by this. Among the above-described configurations, a configuration that executes processing for obtaining area doses may be provided as an area dose obtaining apparatus.

Other Embodiments

Embodiment(s) of the present invention can also be realized by a computer of a system or apparatus that reads out and executes computer executable instructions (e.g., one or more programs) recorded on a storage medium (which may also be referred to more fully as 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-085721, filed Apr. 26, 2018, which is hereby incorporated by reference herein in its entirety.

What is claimed is:

1. A radiographic apparatus, comprising:
a generating unit configured to generate a composite image using a plurality of radiographic images that have been obtained by a plurality of radiation detecting apparatuses through single radiation irradiation by a radiation generating unit;
a determining unit configured to determine a region to be analyzed so as to eliminate an overlap in an overlapping portion arising from a spatial placement of the plurality of radiation detecting apparatuses; and
an obtaining unit configured to obtain an area dose for the composite image by obtaining an area dose for the region to be analyzed determined by the determining unit.

2. The apparatus according to claim 1, wherein the obtaining unit obtains the area dose for the composite image based on a dose at a detection position and an area of the region to be analyzed determined by the determining unit, and
the dose at the detection position is obtained based on an imaging condition for the single radiation irradiation and a distance from the radiation generating unit to the detection position.

3. The apparatus according to claim 2, wherein the obtaining unit uses a dose at a shared detection position with respect to the plurality of radiation detecting apparatuses.

4. The apparatus according to claim 2, wherein the obtaining unit obtains doses that respectively correspond to the plurality of radiographic images based on distances between the radiation generating unit and detection positions that respectively correspond to the plurality of radiation detecting apparatuses.

5. The apparatus according to claim 4, further comprising a storing unit configured to store the composite image and the area dose for the composite image in association with each other.

6. The apparatus according to claim 1, wherein the determining unit extracts the overlapping portion based on position information of the plurality of radiation detecting apparatuses.

7. The apparatus according to claim 1, wherein the determining unit determines the region to be analyzed with respect to each of the plurality of radiographic images so as to eliminate the overlap in the overlapping portion, and
the obtaining unit obtains area doses respectively for the plurality of radiographic images, and obtains the area dose for the composite image by totaling the plurality of area doses obtained for the plurality of radiographic images.

8. The apparatus according to claim 7, wherein the region to be analyzed is one of a region obtained by removing the overlapping portion from an entirety of the radiographic images, a region where radiation irradiation exists in the radiographic images, or a region of an object in the radiographic images.

9. The apparatus according to claim 1, wherein the determining unit eliminates the overlap in the overlapping portion by determining an area of the region to be analyzed with respect to the composite image.

10. The apparatus according to claim 9, wherein the region to be analyzed is one of an entirety of the composite image, a region where radiation irradiation exists in the composite image, or a region of an object in the composite image.

11. An area dose obtaining method used by a radiographic apparatus, the method comprising the steps of:
generating a composite image using a plurality of radiographic images that have been obtained by a plurality of radiation detecting apparatuses through single radiation irradiation by a radiation generating unit;
determining a region to be analyzed so as to eliminate an overlap in an overlapping portion arising from a spatial placement of the plurality of radiation detecting apparatuses; and
obtaining an area dose for the composite image by obtaining an area dose for the determined region to be analyzed.

12. A non-transitory computer-readable storage medium storing therein a program for causing a computer to execute the area dose obtaining method according to claim 11.

* * * * *